(12) United States Patent
Iyer et al.

(10) Patent No.: US 8,350,061 B2
(45) Date of Patent: Jan. 8, 2013

(54) SYNTHETIC ANALOGS OF BACTERIAL QUORUM SENSORS

(75) Inventors: Rashi S. Iyer, Los Alamos, NM (US); Kumkum Ganguly, Los Alamos, NM (US); Louis A. Silks, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/286,661

(22) Filed: Nov. 1, 2011

(65) Prior Publication Data

US 2012/0071430 A1     Mar. 22, 2012

Related U.S. Application Data

(62) Division of application No. 12/551,994, filed on Sep. 1, 2009, now Pat. No. 8,071,790.

(51) Int. Cl.
    *C07D 307/00*     (2006.01)
    *C07D 333/36*     (2006.01)

(52) U.S. Cl. .......................................... 549/321; 549/63

(58) Field of Classification Search .................... 549/63, 549/321
See application file for complete search history.

(56) References Cited

OTHER PUBLICATIONS

Hentzer et al., "Inhibition of Quorum Sensing in *Pseudomonas aeruginosa* Biofilm Bacteria by a Halogenated Furanone Compound", Microbiology, 2002, vol. 148, pp. 87-102.
Essar et al., "DNA Sequences and Characterization of Four Early Genes of the Tryptophan Pathway in *Pseudomonas aeruginosa*", Journal of Bacteriology, Feb. 1990, vol. 172, No. 2, pp. 853-866.
Glessner et al., "Roles of *Pseudomonas aeruginosa* las and rhl Quorum-Sensing Systems in Control of Twitching Motility", Journal of Bacteriology, Mar. 1999, vol. 181, No. 5, pp. 1653-1629.
Reimmann et al., "The Global Activator GacA of *Pseudomonas aeruginosa* PAO Positively Controls the Production of the Autoinducer N-butyryl-homoserine Lactone and the Formation of the Virulence Factors Pyocyanin, Cyanide, and Lipase", Molecular Microbiology, 1997, vol. 24, pp. 309-319.
Ikeda et al., "The Synthesis of Optically Pure Enantiomers of N-Acyl-homoserine Lactone Autoinducers and Their Analogues", Chemistry Letters, 2001, pp. 314-315.
Ishida et al., Inhibition of Quorum Sensing in *Pseudomonas aeruginosa* by N-Acyl Cyclopentylamides, Applied and Environmental Microbiology, May 2007, vol. 73, No. 10, pp. 3183-3188.
De Kievit et al., "Quorum-Sensing Genes in *Pseudomonas aeruginosa* Biofilms: Their Role and Expression Patterns", Applied and Enviromental Microbiology, Apr. 2001, vol. 67, No. 4, pp. 1965-1873.

*Primary Examiner* — Nizal Chandrakumar
(74) *Attorney, Agent, or Firm* — Julie A. Jones; Samuel L. Borkowsky

(57) ABSTRACT

Bacterial quorum-sensing molecule analogs having the following structures:

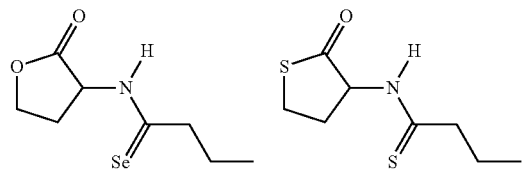

and methods of reducing bacterial pathogenicity, comprising providing a biological system comprising pathogenic bacteria which produce natural quorum-sensing molecule; providing a synthetic bacterial quorum-sensing molecule having the above structures and introducing the synthetic quorum-sensing molecule into the biological system comprising pathogenic bacteria. Further is provided a method of targeted delivery of an antibiotic, comprising providing a synthetic quorum-sensing molecule; chemically linking the synthetic quorum-sensing molecule to an antibiotic to produce a quorum-sensing molecule-antibiotic conjugate; and introducing the conjugate into a biological system comprising pathogenic bacteria susceptible to the antibiotic.

6 Claims, 4 Drawing Sheets

SYNTHETIC ANALOGS OF BACTERIAL QUORUM SENSORS

RELATED APPLICATIONS

This application is a divisional of copending U.S. patent application Ser. No. 12/551,994 entitled "Synthetic Analogs of Bacterial Quorum Sensors," filed Sep. 1, 2009, now allowed, which is incorporated by reference herein.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to synthetic analogs of bacterial quorum sensing molecules, and methods of use thereof.

BACKGROUND OF THE INVENTION

Interbacterial signaling, commonly referred to as quorum sensing (QS) enables bacteria to coordinate their behavior in order to function as a group. Using diffusible chemical signals to initiate a concerted population response depends on the population reaching a threshold number or "quorum". Most microbes require a "quorate population" to manifest an infection in its target host. This bacterial intercellular communication system relies on the production and release of QS molecules that control the expression of multiple target genes which play is pivotal role in virulence and pathogenicity in the host. The most intensively investigated QS signal molecules are acyl-homoserine lactones (AHLs) synthesized by many quorum-sensing, secreting bacteria. AHLs are used to regulate infection, virulence and survival functions. Different bacterial species can produce different AHLs. The basic structure of AHLs consists of a homoserine lactone ring adjoined with an N-acyl chain, ranging in length from 4 or 14 carbons, which may be saturated or unsaturated and may or may not contain a hydroxy- or oxo-group at the 3-carbon position.

To date, AHL-dependent QS circuits have been identified in a wide range of gram-negative bacteria, one example of which is *Pseudomonas aeruginosa*, where the QS circuits regulate various functions to survive in the host. The severity and diversity of infections caused by *P. aeruginosa*, is in part due to its ability to produce a plethora of environment-dependent virulence factors but also due to its recalcitrance to antibiotic treatment when growing in biofilm.

The accepted clinical intervention strategy in bacterial infections is treatment with antibiotics. However, currently prescribed small molecule antibiotics have limitations, especially in advanced infectious states when systemic application cannot provide the required local dose of antibiotics necessary for effective bactericidal action due to compromised half-life of the drug. The efficacy of the antibiotic depends on factors such as selective toxicity, bioavailability of the drug and penetration into the target bacteria. Some very effective antibacterial compounds are unacceptable for human use as they are toxic at their prescribed doses, chiefly due to the fact that current delivery regimens are systemic, thus requiring a whole body dosage to achieve necessary local concentrations. There exists an ongoing need, therefore, for effective treatment of bacterial infections without the disadvantages resulting from traditional systemic application of antibiotics.

SUMMARY OF THE INVENTION

The present invention meets the aforementioned need by providing synthetic analogs of bacterial quorum sensing molecules, specifically, by providing analogs of an autoinducer of *Pseudomonas* quorum sensing system, butanol homoserine lactone (AHL-2). It is believed that these analogs may meet the aforementioned need by either perturbation of critical survival mechanisms by interference with QS-signaling and/or by precise delivery of an antibiotic to its target. In other words, the analogs may act as agonists or antagonists, in that AHL-antagonists may perturb QS-based bacterial communication and consequently attenuate bacterial virulence, while AHL-agonists may be used to manipulate existing bacterial mechanisms for the targeted delivery and enhanced uptake of antibiotics conjugated to analogs of self-derived molecules such as AHLs.

In addition, it is believed that AHL-agonists could be used to induce the premature expression of immunogenic molecules, therefore exposing the bacteria to the host immune system at an early state of infection. The basis for this belief is the observation that *P. aeruginosa* evades detection by the immune system by rapidly down-regulating the transcription and expression of flagellin, a highly immunogenic molecule.

The following describe some non-limiting embodiments of the present invention.

According to a first embodiment of the present invention, a method of reducing bacterial pathogenicity is provided, comprising providing a biological system comprising pathogenic bacteria which produce a natural quorum-sensing molecule; providing a synthetic bacterial quorum-sensing molecule having the structure:

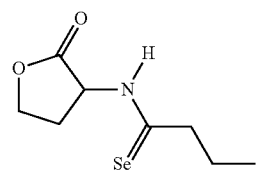

and introducing the synthetic quorum-sensing molecule into the biological system comprising pathogenic bacteria.

According to another embodiment of the present invention, a method of reducing bacterial pathogenicity is provided, comprising providing a biological system comprising pathogenic bacteria which produce a natural quorum-sensing molecule; providing a synthetic bacterial quorum-sensing molecule having the structure:

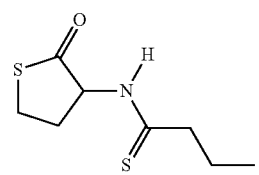

and introducing the synthetic quorum-sensing molecule into the biological system comprising pathogenic bacteria.

According to yet another embodiment of the present invention, a bacterial quorum sensing molecule analog is provided which has the structure:

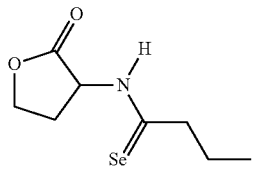

According to yet another embodiment of the present invention, a bacterial quorum-sensing molecule analog is provided which has the structure:

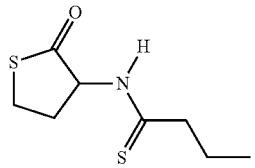

According to yet another embodiment of the present invention, a method of targeted delivery of an antibiotic is provided, comprising providing a synthetic quorum-sensing molecule; chemically linking the synthetic quorum-sensing molecule to an antibiotic to produce a quorum-sensing molecule-antibiotic conjugate; and introducing the conjugate into a biological system comprising pathogenic bacteria susceptible to the antibiotic.

DETAILED DESCRIPTION OF THE INVENTION

Figure 1:
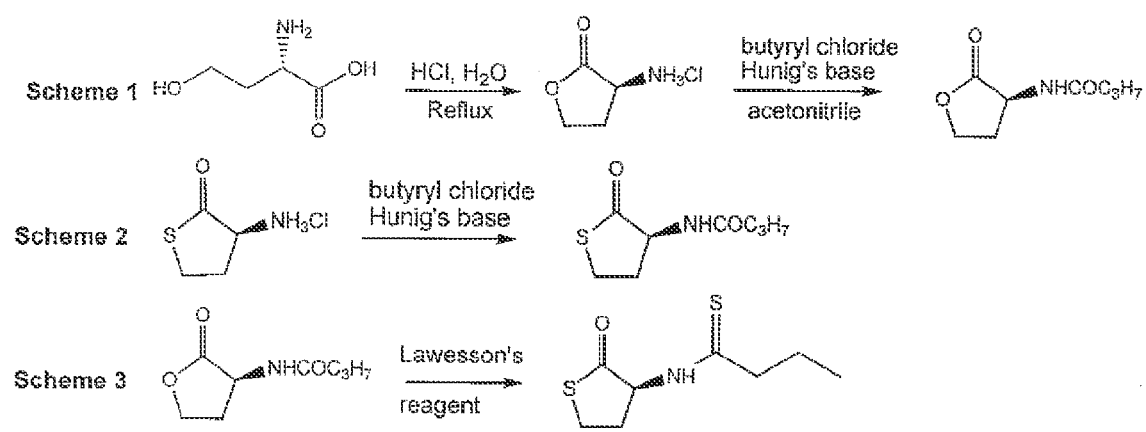
FIG. 1 shows the structures and synthesis of (S)—N-butyryl homoserine lactone (AHL-2) (Scheme 1), (S)—N-butyryl homocysteine thiolactone (QS0108) (Scheme 2), and (S)—N-Thiobutyryl homocysteine thiolactone (QS1207).
Figure 2:
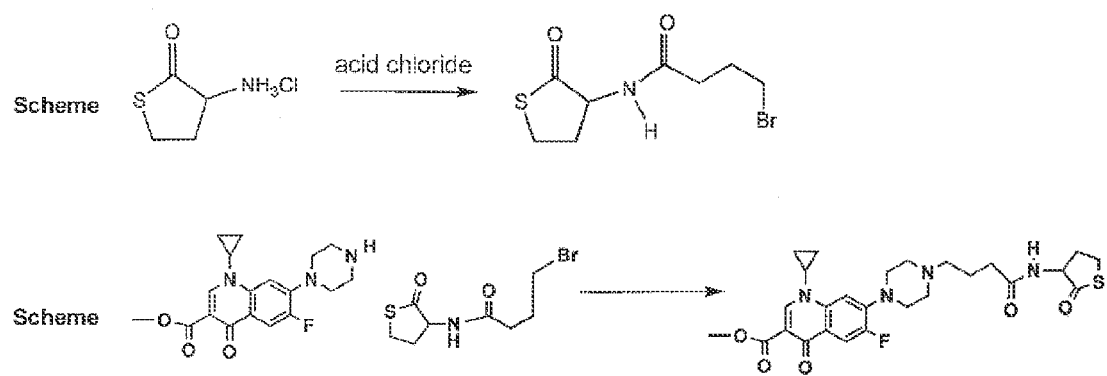
FIG. 2 shows the synthesis of one example of a QS analog-antibiotic conjugate
Figure 3:
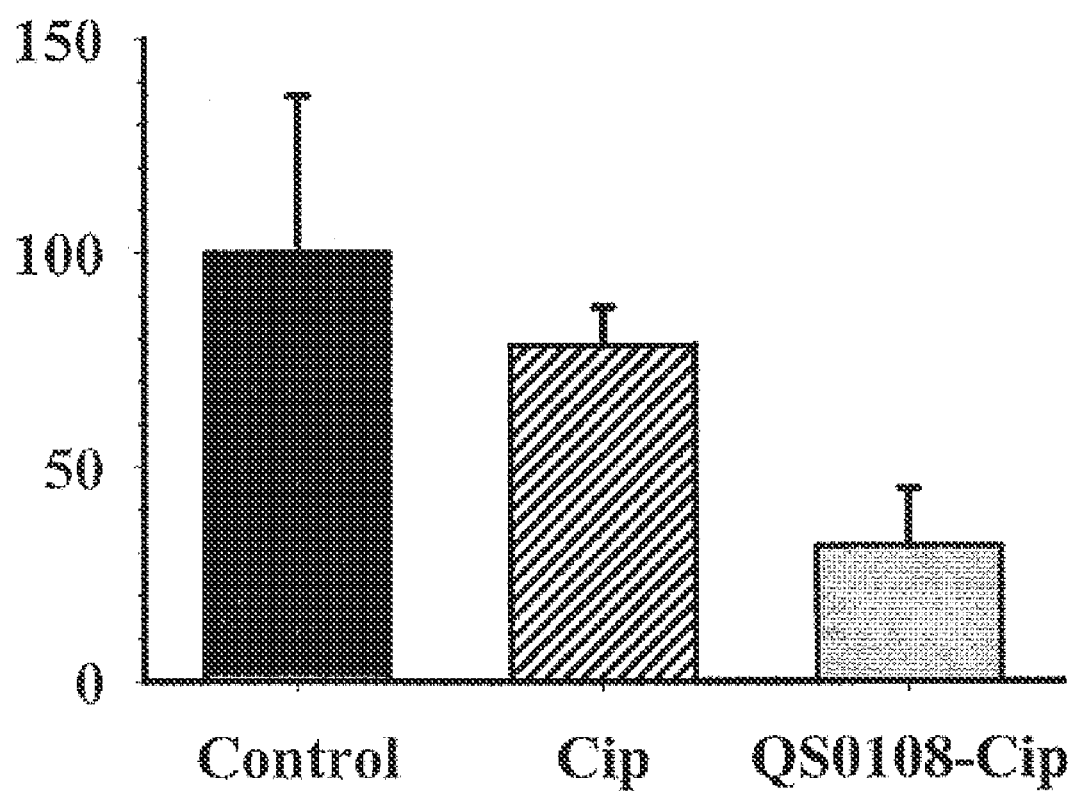
FIG. 3 shows the quantification by CFU (colony forming units) count of persister bacterial cells from biofilms grown on collagen coated coverslips (A), free Cip coated (B) or QS0108-Cip conjugate coated (C) coverslips for 48 hrs. Y-axis represents CFU log/ml.
Figure 4:
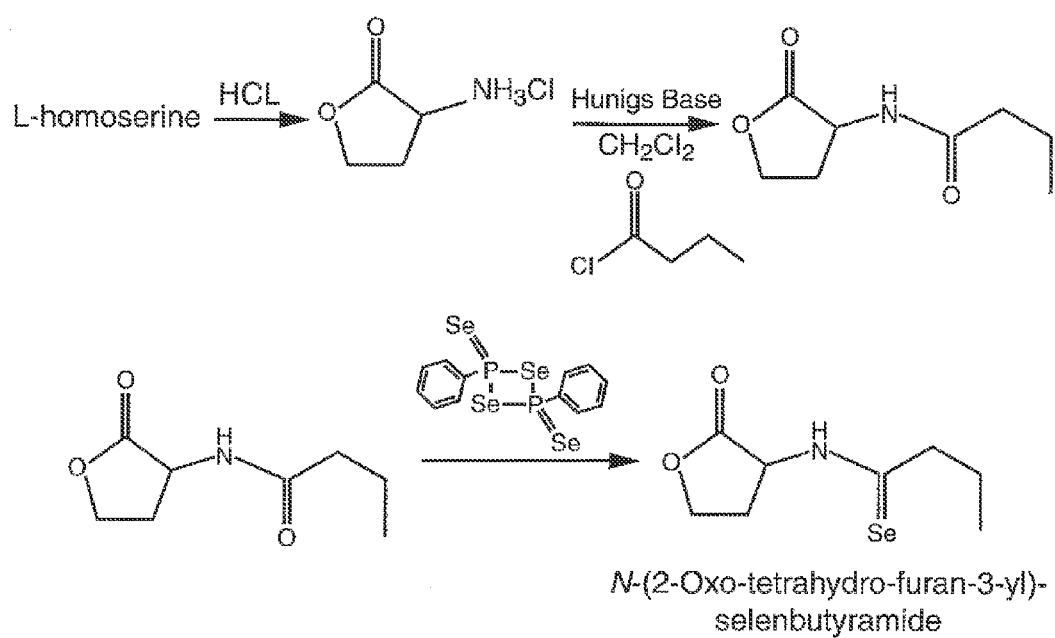
FIG. 4 shows a synthesis of a selenium-containing quorum-sensing analog, N-(2-oxo-tetrahydro-furan-3-yl)-selenobutyramide.

The present invention provides novel, synthetic bacterial quorum-sensing analogs, and methods of using these analogs to reduce bacterial pathogenicity and for targeted delivery of antibiotics. Surface adhered bacterial colonies or biofilms are an important problem in medical and food industries. Bacteria use a chemical language to monitor their quorum and to express virulence factors, which eventually help them in colonization and manifestion of an infection. For example, the LasR-LasI and Rh1R-Rh1I quorum sensing systems of *Pseudomonas aeruginosa* control expression of virulence factors in a population density-dependent fashion. The synthetic analogs described herein have been shown to serve as AHL-agonists by promoting bacterial growth, virulence factor production and biofilm formation. Without wishing to be limited by theory, it is believed that these responses are due either to rapid 'threshold concentrations' reached by the addition of extraneous AHL analogs or to the preferential and enhanced uptake of these molecules by the bacteria. It is further believed that coupling of an antibiotic to these analogs may facilitate targeted delivery of the antibiotic through an otherwise impenetrable biofilm barrier.

Herein, "pathogenic bacteria" means a bacteria capable of causing disease in a host organism when present in sufficient numbers (i.e., a "quorum").

Herein, "synthetic" means a molecule not produced naturally by an organism or found in nature, as opposed to a "natural" molecule, which as used herein means a molecule produced by an organism or biological system.

Herein, "analog" means a synthetic molecule capable of performing one or more of the biological functions that a natural counterpart would perform, such as controlling the expression of target bacterial genes, virulence factor production and biofilm formation. The analog may differ from the natural molecule by a single atom or by multiple atoms.

The synthetic bacterial quorum-sensing molecule of the present invention, also termed "synthetic analogs," "quorum-sensing analogs," or "QS-analogs," are analogs of a natural acyl-homoserine lactone depicted in (I), and biologically mimic the behavior thereof.

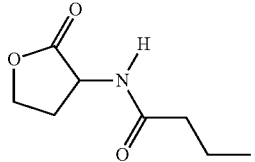

The synthetic analogs of the present invention comprise a lactone ring, either unsubstituted or substituted with a sulfur atom and a side chain either unsubstituted or substituted with a sulfur atom or a selenium atom. Non-limiting examples of suitable bacterial quorum-sensing molecules of the present invention include those depicted in (II), (III) and (IV):

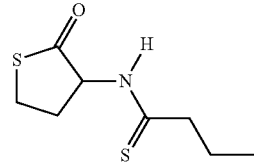

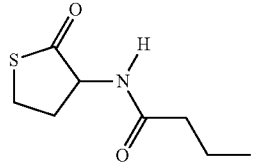

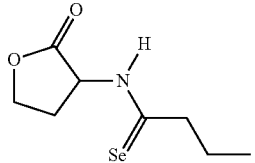

One aspect of the present invention is providing a method of reducing bacterial pathogenicity. As used herein, "reducing bacterial pathogenicity" means that the number of bacteria in a biological system after exposure to a synthetic analog is reduced as compared to a similar (control) biological system which is not exposed to a synthetic analog, or alternatively that the number of bacteria in a biological, system exposed to the synthetic analog increases as compared to a control biological system which is not exposed to a synthetic analog, but does not result in the appearance of measurable indicators of pathogenicity, such as biofilm formation. The method of reducing bacterial pathogenicity comprises providing a biological system which comprises at least one type of pathogenic bacteria which produce a natural quorum-sensing molecule. The biological system may include cultured bacteria, a biological sample, or an organism, including an animal or human. The pathogenic bacteria may be any bacteria which produce a natural quorum-sensing molecule as defined herein. In one embodiment, the pathogenic bacteria are *Pseudomonas aeruginosa* (*P. aeruginosa*), *Yersinia pestis, Yersinia enterocolitca, Yersinia pseudotuberculosis, Burkhotderia cepecia*, and combinations thereof. In another embodiment, the pathogenic bacteria are *Pseudomonas aeruginosa*.

The method further comprises the step of providing a synthetic bacterial quorum-sensing molecule, as described herein. The synthetic bacterial quorum-sensing molecule may be introduced into the biological system by a variety of means that would be known to one of skill in the art, such as by placing the synthetic molecule into a suitable carrier and administering topically, orally, via inhalation or via injection.

Another aspect of the present invention is to provide a method of targeted delivery of an antibiotic to a cell or area of interest in a biological system. By "targeted delivery" is meant delivery of the antibiotic to, for example, a pathogenic bacteria or area of infection, as opposed to systemic delivery of the antibiotic to the entire organism. The method comprises the step of providing any one of the synthetic bacterial quorum-sensing molecules, as described herein and depicted in (II), (III), or (IV). The synthetic quorum-sensing molecule is then chemically linked, whether covalently or non-covalently, to a suitable antibiotic, resulting in a conjugate comprising the quorum-sensing molecule and the antibiotic ("quorum-sensing molecule-antibiotic conjugate," or "conjugate"). The conjugate is then introduced into a biological system which comprises one or more types of pathogenic bacteria susceptible to the antibiotic, wherein "susceptible" means that the antibiotic is known to reduce the number of live bacteria in systems wherein the antibiotic is not linked to a quorum-sensing molecule. It is understood that the pathogenic bacteria naturally produce a quorum-sensing molecule substantially similar to the natural quorum-sensing molecule described herein.

The antibiotic may vary widely, and is limited only by its ability to be chemically linked to the quorum-sensing molecule and by its ability to inactivate or reduce the pathogenicity of the targeted bacteria. In one embodiment, the antibiotic is selected from the group consisting of ciprofloxacin, gentamicin, tobramycin, clarithromycin, piperacillin, and combinations thereof. In another embodiment, the antibiotic is ciprofloxacin. One non-limiting example of a quorum-sensing molecule-antibiotic conjugate (also known as a "cip-conjugate") is depicted in (V):

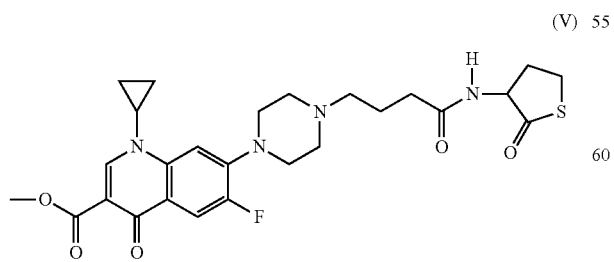

(V)

wherein the —O represents a methoxy group. In the conjugate depicted in (V), the quorum-sensing molecule (II) has been conjugated to an antibiotic, ciprofloxacin. It is to be understood, however, that the structures depicted above in (III) and (IV) may be conjugated to the antibiotic.

EXAMPLES

Synthesis of homoserine lactone (AHL-2), analogs (QS1207; QS0108); (S)-Homoserine lactone hydrochloride: (S)-homoserine (25 g, 0.21 mol) was dissolved in aqueous hydrochloric acid (2.4 M, 322 mL, 0.97 mol, 4.6 equiv). The solution was refluxed for 3 h, and stirred at ambient temperature overnight. Most of the solvent was removed azeotropically with ethanol. Following crystal formation the solution was cooled on ice. The resulting solid was filtered and rinsed three times with cold ethanol. The filtrate was concentrated and cooled, producing additional homoserine lactone. The process was repeated 2 more times. After leaving the white powder on high vacuum line overnight, 24 g (83% yield.) of homoserine lactone hydrochloride was obtained. $^1$H NMR (D2O) δ 4.59 (t, J=9.2 Hz, 1H), 4.43 (m, 2H), 2.76 (m, 1H), 2.42 (m, 1H), $^{13}$C NMR (D2O) δ 178.3, 68.3, 49.4, 27.6.

(S)—N-butyryl homoserine lactone (AHL-2): (S)-homoserine lactone (0.100 g, 0.726 mmol) was dissolved in 5 mL of acetonitrile. N,N-diisopropylethyl amine (0.32 mL, 1.8 mmol) was added, followed by butyrylchloride (0.15 mL, 1.4 mmol). The reaction was stirred overnight. The acetonitrile was evaporated and the crude product was purified by flash chromatography using 80% ethyl acetate-hexanes. 0.1 g of white crystals was obtained (81% yield) (FIG. 1; Scheme 1). $^1$H NMR (CDCl$_3$) δ 6.72 (d, J=6.2 Hz, 1H), 4.58 (m, 1H), 4.42 (app t, J=8.1 Hz, 1H), 4.24 (m, 1H), 2.71 (m, 1H), 2.20 (m, 3H), 1.63 (sex, J=7.4 Hz, 2H), 0.91 (t, J=7.4 Hz, 3H). $^{13}$C NMR (CDCl3) δ 175.8, 173.6, 65.9, 48.8, 37.8, 29.7, 18.8, 13.5 (16)

(S)—N-butyryl homocysteine thiolactone (QS0108): (S)-homocysteine thiolactone (0.23 g, 1.5 mmol) was added to 5 mL of methylene chloride. N,N-diisopropylethyl amine (0.32 mL, 1.8 mmol) was added, followed by butyrylchloride (0.15 mL, 1.4 mmol), at ambient temperature. The reaction was stirred overnight. The reaction mixture was then evaporated and the crude product was purified by flash chromatography using 30% ethyl acetate hexanes. 0.14 g of pale yellow white crystals were obtained (50% yield) (FIG. 1; Scheme 2), $^1$H NMR (CDCl3) δ 6.56 (d, J=6 Hz, 1H), 4.6 (m, 1H), 3.33 (m, 1H), 3.23 (m, 1H), 2.78 (m, 1H), 2.20 (t, J=7 Hz, 2H), 1.97 (m, 1H), 1.66 (sex, J=7 Hz, 2H), 0.93 (t, J=7 Hz, 3H). $^{13}$C NMR (CDCl3) δ 205.9, 173.7, 59.7, 38.5, 32.4, 27.8, 19.1, 13.8.

(S)—N-Thiobutyryl homocysteine thiolactone (QS1207): The (S)—N-butyryl homoserine lactone (0.97 g, 5.6 mmol) was placed in a 100 mL round bottom flask and 50 mL of toluene (stock) was added. The flask was then fitted with a reflux condenser and purged with argon. Lawesson's reagent (2.26 g, 5.6 mmol) was then added as a solid. The suspension was stirred until homogenous and brought to reflux with a heating mantle. The reaction was periodically monitored by TLC (35% ethyl acetate/hexane; v/v). After 4 hours the reaction was cooled and the volume was reduced to around 3 mL. Purification by flash column chromatography gave rise to a crystalline material (0.3 g, 26% yield) (FIG. 1; Scheme 3). $^1$H NMR (CDCl3) δ 7.60 (bs, 1H), 4.6 (m, 1H), 5.15 (m, 1H), 3.31 (m, 2H), 2.70 (1, J=7 Hz, 2H), 1.95 (m, 1H), 1.90 (m, 2H), 0.96 (t, J=7 Hz, 3H), $^{13}$C NMR (CDCl3 δ=77.0) δ 207.6, 205.2, 64.0, 48.2, 30.2, 27.5, 22.6, 13.1. (FIG. 1, Scheme 3).

Synthesis of conjugate (QS0108-Cip): (D,L)-4-bromo-N-(2-oxotetrahydrothiophen-3-yl) butanamide. D,L-homocysteine thiolactone hydrochloride (5.2 g, 34 mmol) was dissolved in water and covered with ethyl acetate. The solution was cooled to 0° C. and the acid chloride (7.06, 38 mmol) was added dropwise. Subsequently 1N NaOH was added dropwise (44.2 mmol). The mixture was stirred for 1 h during which the temperature of the reaction warmed to ambient temperature. No precipitate was observed, however, TLC analysis (10% MeOH/methylene chloride; v/v) indicated all the starting material (dissolved in saturated $NaHCO_3$ before spotting the TLC) had been consumed. The reaction mixture was extracted several times with ethyl acetate. The ethyl acetate was dried over $Na_2SO_4$, filtered, and the solvent was removed in vacuo to give 2.2.4 g of an off-white solid (25% yield).

Ciprofloxacin conjugate to (D,L)-4-bromo-N-(2-oxotetrahydrothiophen-3-yl)butanamide: In a 25 mL round bottom flask, under argon, was placed the (S)-4-bromo-N-(2oxotetrahydrothiophen-3-yl)butanamide and the methyl ester of Cip. 10 mL of acetonitrile was added. The solution was stirred for 5 min then the $K_2CO_3$ was added. The mixture was then stirred for 24 h at ambient temperature. The solution was then warmed and stirred for an additional 24 h. The volatile components were removed and the materials subjected to purification by column chromatography to give an off white powder. $^1$H NMR (CDCl3) δ. HRMS C26H32O5N4F1 S1 531.20667 (error +/−0.992 ppm). Ciprofloxacin was obtained from Sigma Aldrich (St. Louis, Mo.). Synthesis of N-(2-oxtetrahydrofuran-3-yl)butaneselenoamide. In a single necked 14/20 round bottom flask was placed a magnetic stir bar, 0.5000 g of N-(2-oxotetrahydrofuran-3-yl)butyramide (2.920 mmol), and 1.000 g of Woolins reagent (1.88 mmol). Dry toluene (20 mL) was then added. The flask was then fitted with a reflux condenser and placed under argon. The system was purged with argon for ~30 min. The mixture was then brought to a gentle reflux and stirred overnight. The reaction was cooled and the solution was then added to silica gel column for purification. Using a 30% ethyl acetate/hexane mixture (v/v) 0.330 g of the selenoamide was isolated. Yield=48.2%. $^1$H d (CDCl$_3$) 0.97 (t, J=7 Hz, 3H), 1.86 (s, J=7.5 Hz, 1H), 2.17 (m, 1H), 2.75 (dd, J=1.8, 6.3 Hz, 2H), 3.25 (m, 1H), 4.40 (m, 1H), 4.53 (t=9.3 Hz, 1H), 8.8 (bs, 1H). $^{13}$C d (CDCl$_3$) 215.0, 175.2, 66.9, 57.2, 52.4, 29.3, 23.3, 13.3. $^{77}$Se d (CDCl$_3$) 304.4.

Bacterial strains: *Pseudomonas aeruginosa* PAO-1 (wild type; #BAA47) was obtained from ATCC (Manassas, Va.). *Pseudomonas* mutant strains JP-1 (−/−C12HSL); PDO-100 (−/−C4HSL) and JP-2 (−/C$_{12}$HSL & C$_4$HSL) were obtained from Dr. B. Iglewski, University of Rochester, N.Y. Strains of *P. aeruginosa* and *B. cepacia* were grown at 37° C. with shaking in LB medium. *Pseudomonas* broth (ref) was used for production of pyocyanin. Wild type and mutant strains were stored at −80° C.; in glycerol stock. Unless otherwise stated in all experiments bacteria were grown to their log phase (O.D 0.4 at A600; corresponding CFU 5×10$^7$/mL) and then inoculated into the medium containing either 10 μM of synthetic autoinducer homoserine lactone (C$_4$HSL; AHL-2) or the analogs (QS1207 & QS0108).

Chemicals for AHL synthesis: All chemicals were purchased from Sigma Aldrich (St. Louis, Mo.)

Biofilm formation assay: Static biofilms were formed on chambered cover glass (#1 borosilicate) by allowing growth of the bacteria for 48 hrs at 37° C. Chambers were inoculated with overnight grown culture containing about 5×10$^7$ bacteria, and were then supplemented with either 10 μM. AHL-2 or QS-1207 or QS-0108. Biofilms were stained by a BacLight™ kit (Invitrogen) and were imaged by an Olympus™ Confocal Microscope (FV300), Olympus™ CCD camera and images were analyzed by Olympus Fluoview™ software.

Motility assays: Wild type and mutant strains of bacteria were allowed to grow for 24 hrs in presence of either AHL-2 or the analogs QS-1207 or QS-0108 and then examined for changes in twitching motility and flagellar motility. For twitching motility studies, plates with LB agar (1%) were poured to an average depth of 3 mm and dried briefly. The strains to be tested were stab inoculated to the bottom of the petri dish and incubated for 24 hrs at 37° C. After the incubation period the zone between the agar and the bottom of the petri dish (the "twitch zone"), was measured as described in Glessner, A. et al., Journal of bacteriology, 181, 1623-1629 (1999). Flagellum mediated motility was assayed by inoculating the treated bacteria to the center of a LB agar (0.3%) plate. After 24 hrs of incubation the plates were inspected for radial zones of bacterial growth (swim zone) indicating a motile response.

Protease activities: Total protease production of AHL-2 and analog treated wild type and mutant strains were assayed on skim milk agar plate containing blood agar base. Ultra high temperature treated skim milk was added to sterilized blood agar base. Bacterial cultures after overnight treatment with AHL-2 and QS analogs were deposited on milk agar plate. Following incubation with bacteria, the diameters of the clear zones were measured as an indicator of proteolytic activities as described in Reimmann, C. et al. Molecular microbiology, 24, 309-319 (1997).

Pyocyanin assay: Cultures grown in pseudomonas broth as described in Essar, D. W. et al, Journal of bacteriology 172, 884-900 (1990) to maximize pyocyanin production, were extracted with 3 ml of chloroform and then re-extracted into 1 ml of 0.2N HCl to give a deep red solution. The absorbance was measured at 520 nm, also as described in Essar et al.

Expression of pyocyanin mRNA: *P. aeruginosa* wild type (PAO-1) and mutant strains (JP-1. PDO-100 and JP-2) were grown in the presence of either AHL-2, QS-1207 or QS-0108 and RNA sampling points were established. Total RNA from three independent cultures were extracted using QIAGEN™ kit. A preliminary phase of destruction of bacterial envelope was achieved by incubating in a solution of lysozyme (1 mg/ml) for 3-5 min at room temperature. One step quantitative real time RT-PCR was used to quantitate mRNA. Primer for Phz1 gene (a key player in pyocyanin biosynthesis) was obtained from Sigma Aldrich (St. Louis, Mo.) following the template published by Lenz, A. P. et al., Applied and environmental microbiology, 74, 4463-4471 (2008). Primer and probe concentrations were determined by performing the optimization protocols recommended by the manufacturer TaqMan™ SYBR Green based RT-PCR was used to measure the house keeping 16sRNA gene. Each sample was assayed in triplicate and statistical analysis was done by two-tailed Mann-Whitney test.

Antimicrobial efficacy testing: The minimal inhibitory concentration (MIC) of free ciprofloxacin (Cip) vs. QS-0108 conjugated ciprofloxacin (QS-0108-Cip) in logarithmic planktonic growth of wild type *P. aeruginosa* PAO-1 was tested according to standard NCCLS microdilution method (22). Exponentially growing bacteria were incubated with free vs. conjugated Cip at concentrations ranging from 1-50 μM for 3 h.

Assessment of biofilm disrupting activity of QS-0108-Cip conjugate: The susceptibility of PAO-biofilms was tested by either pre or post treatment of free Cip vs. QS-0108-Cip at sub MIC doses (10-25 µM) of the conjugate. In the "pre-treatment" group biofilm was initiated in presence of free or conjugated Cip, whereas in the "post-treatment" group drugs were applied after 24 hours of biofilm formation. Biofilms were stained with Bac-Light Live/Dead stain at 48 hrs and observed using confocal microscopy. In another experiment PAC)-1 biofilms were grown up to 72 hrs and then exposed to free vs. conjugated Cip at 25 µM for 24 hrs. In a separate experiment collagen treated chamber cover slips were coated with free vs. conjugated Cip. The coverslips were washed to remove excess unadhered antibiotics and PAO-1 biofilms were grown for 24 hr, stained and visualized under a Zeiss™ epifluorescent microscope. Quantification of these experiments was done by measuring CFU count.

Viability and biofilm formation in bacteria treated with the selenium-containing bacterial quorum-sensing molecule depicted in (IV) above:

Strains of *Yersinia pestis, Yersinia enterocolitica* and *Yersinis pseudomonas* were grown for 48 hrs in LB medium containing either 10M of AHL-1, 100 µM selenium alone or with the compound depicted in (IV). All three control samples formed a dense multilayer biofilms of varying thickness. Cultures treated with free selenium had no notable inhibitory effect on biofilm formation or growth of the bacteria. In contrast, treatment of these bacteria with (IV) significantly inhibited biofilm formation and viability of biofilm-growing bacteria. The cultures treated with (IV) formed relatively thin biofilms, if any at all, and lacked the three-dimensional architecture compared to control untreated biofilm cultures. These results indicate that the biofilm inhibition observed in bacterial samples treated with (IV) was not due to selenium but to the conjugate itself.

Infection of human cells by *Pseudomonas aeruginosa*: Studies also were performed with *Pseudomonas aeruginosa* in A549 human lung epithelial cells. Cells were either treated with *Pseudomonas aeruginosa* alone, pretreated with the selenium-containing compound depicted in (IV), followed by exposure to *Pseudomonas aeruginosa*, and treated with PA followed by post-treatment with (IV). An increase in the viability of cells was observed in cells pre- and post-treated with (IV). These results indicate that QS-0208 prevented the infection of cells by *Pseudomonas aeruginosa* and appeared to protect the cells from *Pseudomonas aeruginosa* pre- or post-exposure.

In all embodiments of the present invention, all ranges are inclusive and combinable. All numerical amounts are understood to be modified by the word "about" unless otherwise specifically indicated. All documents cited in the Detailed Description of the invention are, relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing bacterial pathogenicity comprising:
    a) providing a biological system comprising pathogenic bacteria which produce a natural quorum-sensing molecule;
    b) providing a synthetic bacterial quorum-sensing molecule having the structure:

c) introducing the synthetic quorum-sensing molecule into the biological system comprising pathogenic bacteria.

2. The method of claim 1, wherein the pathogenic bacteria are selected from the group consisting of *Pseudomonas aeruginosa, Yersinia pestis, Yersinia enterocolitca, Yersinia pseudotuberculosis, Burkholderia cepecia*, and combinations thereof.

3. The method of claim 1, wherein the pathogenic bacteria is *Pseudomonas aeruginosa*.

4. A method of reducing bacterial pathogenicity comprising:
    a) providing a biological system comprising pathogenic bacteria which produce a natural quorum-sensing molecule;
    b) providing a synthetic bacterial quorum-sensing molecule having the structure:

c) introducing the synthetic quorum-sensing molecule into the biological system comprising pathogenic bacteria.

5. The method of claim 4, wherein the pathogenic bacteria are selected from the group consisting of *Pseudomonas aeruginosa, Yersinia pestis, Yersinia enterocolitca, Yersinia pseudotuberculosis, Burkholderia cepecia*, and combinations thereof.

6. The method of claim 5, wherein the pathogenic bacteria is *Pseudomonas aeruginosa*.

* * * * *